United States Patent [19]

Wiedemann et al.

[11] 4,141,909
[45] Feb. 27, 1979

[54] PROCESS FOR THE OPTIMIZATION OF THE MANUFACTURE OF PHTHALIC ACID ANHYDRIDE

[75] Inventors: Otto Wiedemann, Munich-Geiselgasteig; Josef Sedlmeier, Munich, both of Fed. Rep. of Germany

[73] Assignee: Wacker-Chemie GmbH, Munich, Fed. Rep. of Germany

[21] Appl. No.: 873,393

[22] Filed: Jan. 30, 1978

[30] Foreign Application Priority Data

Mar. 15, 1977 [DE] Fed. Rep. of Germany ....... 2711289

[51] Int. Cl.$^2$ .......................................... C07D 307/89
[52] U.S. Cl. .............................. 260/346.4; 260/346.7
[58] Field of Search ........................... 260/346.4, 346.7

[56] References Cited

U.S. PATENT DOCUMENTS

| | | | |
|---|---|---|---|
| 3,178,452 | 4/1965 | Smith et al. | 260/346.4 |
| 3,306,915 | 2/1967 | Vrbaski | 260/346.4 X |

FOREIGN PATENT DOCUMENTS 1939925  2/1971  Fed. Rep. of Germany ........ 260/346.4

*Primary Examiner*—Richard L. Raymond
*Attorney, Agent, or Firm*—Hammond & Littell

[57] ABSTRACT

A process for the optimization of the manufacture of phthalic acid anhydride comprising the steps of subjecting o-xylene to a gas phase oxidation over catalysts containing vanadium oxide and titanium oxide at temperatures of from 300° C. to 500° C., wherein said temperature is at least 5° C. to 20° C. below the optimum temperature for conversion to phthalic acid anhydride with less than 0.1% by weight content of phthalide, recovering an impure phthalic acid anhydride containing more than 0.1% by weight of phthalide, subjecting said impure phthalic acid anhydride to countercurrent crystallization, and recovering phthalic acid anhydride crystals having a content of less than 0.1% by weight of phthalide.

3 Claims, No Drawings

PROCESS FOR THE OPTIMIZATION OF THE MANUFACTURE OF PHTHALIC ACID ANHYDRIDE

BACKGROUND OF THE INVENTION

The present invention concerns an optimization of the manufacture of phthalic acid anhydride (PA) to increase the yield of phthalic acid anhydride and to extend the life of the catalyst by combining a process step of the partial oxidation of o-xylene in the gas phase over solid bed catalysts that contain vanadium oxide and titanium oxide at temperatures below the optimum salt bath temperature, with a purification process step of countercurrent crystallization.

Processes for the manufacture of PA are known to the man skilled in the art and substantially consist in the gaseous oxidation of o-xylene where the o-xylene/air mixture is passed through tube assembly reactors filled with catalysts that contain vanadium oxide and titanium oxide. In addition to the exothermic oxidation to form PA, undesired by-products are produced, such as carbon monoxide and carbon dioxide, as a result of excess oxidation and also, for example, tolulyl aldehyde and phthalide as a result of insufficient oxidation. The underlying problem of the industrial manufacture of PA was, therefore, so to select the reaction parameters that excess or insufficient oxidation are avoided as far as possible. Particular attention was paid to keeping the phthalide content of the PA product as low as possible as this impurity presents special difficulties in the purification of PA. The reaction conditions over the catalyst are so selected that the lowest possible phthalide contents are obtained in the reaction product. The purity of the product is correlated with an increase in the temperature of the salt bath in the reactor. The optimum salt bath temperature is usually that temperature at which PA with phthalide contents of from 0.01% to 0.1% by weight are obtained in the crude product. This means, however, that the temperature stress reduces the life of the catalysts in the long term and the presence of such small amounts of the insufficiently oxidized product, phthalide, results in excess oxidation of the o-xylene used with an overall loss in yield.

The purification of the crude PA is usually effected by refluxing with the addition of various neutralizing or oxidizing substances or by distillation. In practice, from the crude anhydride, approximately 2 parts or more of PA are lost per part of phthalide to be removed. Furthermore, purification by distillation entails considerable energy costs.

OBJECTS OF THE INVENTION

An object of the invention is so to optimize the present method of manufacture that, on the one hand, the conditions of catalysis are relaxed by a low salt bath temperature and the life of the catalyst is increased, and on the other hand, that more pure PA, measured against the o-xylene used, is obtained on balance per completed process.

Another object of the present invention is the development of a process for the optimization of the manufacture of phthalic acid anhydride comprising the steps of subjecting o-xylene to a gas phase oxidation over catalysts containing vanadium oxide and titanium oxide at temperatures of from 300° C. to 500° C., wherein said temperature is at least 5° C. to 20° C. below the optimum temperature for conversion to phthalic acid anhydride with less than 0.1% by weight content of phthalide, recovering an impure phthalic acid anhydride containing more than 0.1% by weight of phthalide, subjecting said impure phthalic acid anhydride to countercurrent crystallization, and recovering phthalic acid anhydride crystals having a content of less than 0.1% by weight of phthalide.

These and other objects of the invention will become more apparent as the description thereof proceeds.

DESCRIPTION OF THE INVENTION

The subject of the invention is an optimization of the manufacture of phthalic acid anhydride by combining a gas phase oxidation of o-xylene over catalysts that contain vanadium pentoxide and titanium dioxide in tubular reactors at salt bath temperatures of between 300° C. and 500° C. with a subsequent separation of the reaction mixture, characterized in that first, crude phthalic acid anhydride is manufactured by oxidation at temperatures of 5° C. to 20° C. below the optimum salt bath temperature and is then purified in a second step by countercurrent crystallization.

More particularly, the present invention relates to a process for the optimization of the manfacture of phthalic acid anhydride comprising the steps of subjecting o-xylene to a gas phase oxidation over catalysts containing vanadium oxide and titanium oxide at temperatures of from 300° C. to 500° C., wherein said temperature is at least 5° C. to 20° C. below the optimum temperature for conversion to phthalic acid anhydride with less than 0.1% by weight content of phthalide, recovering an impure phthalic acid anhydride containing more than 0.1% by weight of phthalide, subjecting said impure phthalic acid anhydride to countercurrent crystallization, and recovering phthalic acid anhydride crystals having a content of less than 0.1% by weight of phthalide.

It can sometimes be of advantage to carry out purification by refluxing with the addition of neutralizing or oxidizing substances in combination with purification by distillation before the countercurrent crystallization purification step.

By means of the optimized process according to the invention, it becomes possible to manufacture pure PA containing less than 0.1% by weight of phthalide and, at the same time, to increase the yield of PA, measured against the o-xylene used, and in so doing, to improve the life of the catalyst by relaxing the reaction conditions.

Although phthalide is not the only impurity in crude PA, the content of phthalide, simply as a result of difficult separation and its significance for the "heat-haze number" can be used as an index of the usability of crude PA. For this reason, the optimum reaction conditions are those which result in the lowest possible contamination of crude PA by the product of insufficient oxidation, phthalide.

On the other hand, it is necessary so to control the catalytic oxidation reaction so that losses as a result of excess oxidation in the form of carbon monoxide and carbon dioxide are avoided. Suitable catalysts for catalytic oxidation are all those that contain vanadium pentoxide and titanium oxide, and that are usually suitable for the manufacture of PA from o-xylene in the gas phase at temperatures of between 300° C. and 500° C. The catalysts generally consist of a catalyst carrier, such as, for example, quartz, porcelain, aluminum oxide, silica, earthenware, pumice stone or silicates, such as for example, magnesium silicate. The specific surface area of the carrier should be as small as possible. It has been found that catalyst balls of approximately 8 mm are particularly suitable for the tubes used in most reaction furnaces, which tubes have an internal diameter of 25 mm. A coating with mixtures of titanium dioxide and vanadium pentoxide in amounts of 30 to 60 gm per liter has proved particularly suitable for the carriers.

It is advantageous to select a catalyst, the coating of which, after being prepared from either anatase with a BET-surface area of 7 to 11 m$^2$/gm or hydrated titanium dioxide with a BET-surface area of more than 100 m$^2$/gm, or vanadium pentoxide, and after being tempered for five hours at 400° C. has a BET-surface area of 15 to 100 m$^2$/gm, preferably 25 to 50 m$^2$/gm. Such catalysts are disclosed in German published Application No. DOS 21 06 796.

To control the temperature, the catalyst filled tubes are surrounded with a salt melt. The hourly charge per liter of catalyst is generally 1.5 to 6 Nm$^3$ of air which contains up to 150 gm, in particular 40 to 100 gm, of o-xylene per Nm$^3$. The gaseous mixture is advantageously preheated to 150° C. to 300° C. and passed through the tubes, where the highest temperature (hot spot), which should not exceed 500° C., occurs in the first third of the catalyst layer. The optimum salt bath temperature is generally between 300° C. and 410° C. depending on the specific surface area and the charge of the catalyst, and is catalyst-specific. For each catalyst charge it is necessary to determine the respective optimum salt bath temperature. Since the effectiveness of the catalyst decreases during the operation, the optimum temperatures alter, becoming somewhat higher during the course of time.

According to the invention, the process is carried out at a salt bath temperature of 5° C. to 20° C. below the optimum temperature. These reaction conditions are recognized by the phthalide content in crude PA rising above 0.1% to a maximum of 2% by weight. Although crude PA obtained in this manner has a higher phthalide content compared to the PA manufactured under optimum reaction conditions, in continuous operation, for every 5° C. decrease in temperature, there is an increase in the effective yield of PA, based on the o-xylene used, of up to 1% by weight. The lowering of the salt bath temperature in comparison to the optimum temperature is limited, however, because at too low a temperature, the "furnace goes out," the exothermic reaction is extinguished, and a disruptive discharge of o-xylene occurs, which is unacceptable purely on the ground of environmental pollution.

A further variation of the process for the oxidation stage is, after starting up the reactor, to begin the catalytic reaction under the optimum reaction conditions, but then not to effect an increase in the salt bath temperature, which is usually necessary owing to the aging of the catalyst. This inevitably leads in time to the operation of the catalytic reaction necessary according to the invention adjusting itself to below the optimum temperature.

The crude product obtained in ribbed tube condensors is then subjected to purification consisting solely of countercurrent crystallization or of a combination of a pre-treatment with the purification step of countercurrent crystallization. The pre-treatment of the crude product may, for example, consist in the crude PA being refluxed, after the addition of 0.01% by weight of sodium carbonate for six to fifteen hours, and then vacuum distilled at 200 to 400 Torr.

To separate the by-products, the crude PA is then subjected to a purification step in a crystallization column. Such crystallization columns are generally known and are described, for example, in "Ullmann Enzyklopadie der technischen Chemie," 4th Edition, Volume 2, page 689, or in U.S. Pat. No. 3,645,699.

All crystallization columns have more or less the following flow plan in common. The crude PA is introduced in a molten state into the purification column in the section which lies approximately between the purification zone and the discharge zone and flows in countercurrent to the separated crystals. Crystallization begins at a certain temperature, at which the crystals grow, while they are transported by a transport mechanism, e.g., a spiral or a scraper ribbon conveyer or by gravity alone, and may be collected in one portion of the apparatus, melted and removed. The impurities in the supply and the pure product can be determined by means of a gas chromatogram.

Countercurrent crystallization of phthalic acid anhydride is generally carried out in a temperature range of approximately 10° C. to 30° C. below the melting point of the mixture in the freezing-out zone. By means of countercurrent crystallization, it is possible to manufacture, with acceptable energy expenditure, pure PA containing less than 0.1% by weight of phthalide.

By means of the process according to the invention, it is furthermore possible to isolate phthalide in the form of useful chemicals on a large scale.

The following examples illustrate the practice of the invention without being limitative in any respect.

EXAMPLE 1

5 Liters of non-porous aluminum silicate balls having an average diameter of 8 mm (7.6 to 8.7 mm) were sprayed in a coating drum at 150° C. with a suspension of TiO$_2$ and V$_2$O$_5$. The suspension contained, per liter, 50 gm of V$_2$O$_5$ and 400 gm of TiO$_2$ (anatase with a BET-surface area of 20 m$^2$/gm) as well as 10 gm of saccharose as a binding agent. Coating of the carrier was stopped after 260 gm of coating had been applied to the 5 liters of balls.

The catalyst manufactured in this manner was charged into two single-tube furnaces (tube length 3.2 m, diameter 25 mm) to a height of 260 cm. The salt bath surrounding the tubes was heated to 375° C. and a mixture of 4 Nm$^3$ of air and 165 gm of o-xylene vapor (96% strength o-xylene) was fed through each tube per hour. The phthalic acid anhydride that formed was condensed in transverse ribbed tube condensors (gas exit temperature 61° C.). The phthalide content of the separated product was at first 0.01% by weight and rose during the course of six weeks to 0.1 to 0.12%. Then, in one furnace, the salt bath temperature was raised in two stages to 378° and 380° C. As a result, the phthalide content reverted to 0.01%. During the next twelve months the phthalide content slowly rose to 0.04% whereas the product of the furnace that continued to operate unchanged at 375° C. contained 0.57% of phthalide. The average yield obtained over 12 months was, at 380° C., 109 kg of separated phthalic acid anhydride based on 100 kg of pure o-xylene charged. In contrast to this, at 375° C., 110.8 kg per 100 kg charged were obtained.

The crude product obtained at a salt bath temperature of 375° C. was refluxed for twelve hours after the addition of 0.01% of sodium carbonate and then vacuum distilled at 300 Torr. The distillate was further purified in a crystallization column according to Schildknecht ("Ullmanns Encyclopadie der technischen Chemie," 4th Edition, Volume 2, page 689). With the apparatus operation at a rate of 30 rev/min, 95 gm per hour of molten material were added at a temperature of 136° C. 60 gm of pure product per hour were drawn off from the lower end. The impurities in the supply and the pure product were determined with the aid of a gas chromatogram.

|  | Supply | Pure Product |
| --- | --- | --- |
| Maleic acid % | 0.07 | 0.01 |
| Benzoic acid % | 0.09 | 0.02 |
| Phthalide % | 0.52 | 0.08 |

EXAMPLE 2

A catalyst taken from an industrial plant after 3½ years of operation (quartz chips of 6 to 10 mm, 2.6% coating consisting of 0.5% of $V_2O_5$, 2% of $TiO_2$, the remainder $Fe_2O_3$ and silicates, BET-surface area of the coating 11.2 $m^2/gm$) were charged into a single-tube furnace to a height of 2.8 m. At a salt bath temperature of 405° C. and a charge of 4 $Nm^3$ of air per hour and 42 gm of 96% strength o-xylene per $Nm^3$, a crude phthalic acid annhdride product having 0.52% of phthalide was obtained. The yield was 107 kg of separated phthalic acid anhydride based on 100 gm of pure o-xylene charged. It was possible to use the catalyst for another year under the operating conditions mentioned. During this time, the phthalide content rose to 0.85%. The product obtained was first pre-purified with the crystallization column described in Example 1 and then distilled at 300 Torr. The pure PA contained 0.09% of phthalide and less than 0.01 of maleic acid anhydride and benzoic acid.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the optimization of the manufacture of phthalic acid anhydride comprising the steps of subjecting o-xylene to a gas phase oxidation over catalysts containing vanadium oxide and titanium oxide at temperatures of from 300° C. to 500° C., wherein said temperature is at least 5° C. to 20° C. below the optimum temperatute for conversion to phthalic acid anhydride with less than 0.1% by weight content of phthalide, recovering an impure phthalic acid anhydride containing more than 0.1% by weight of phthalide, subjecting said impure phthalic acid anhydride to countercurrent crystallization, and recovering phthalic acid anhydride crystals having a content of less than 0.1% by weight of phthalide.

2. The process of claim 1 wherein said gas phase oxidation step is conducted in a tubular reactor immersed in a molten salt bath and said temperatures are the salt bath temperatures.

3. The process of claim 1 wherein an intermediate purification step of refluxing the impure phthalic acid anhydride in the presence of sodium carbonate and subsequently distilling is conducted prior to said countercurrent crystallization step.

* * * * *